United States Patent [19]

Knifton

[11] Patent Number: 4,616,097

[45] Date of Patent: Oct. 7, 1986

[54] PROCESS FOR LOW PRESSURE SYNTHESIS OF ETHYLENE GLYCOL FROM SYNTHESIS GAS PLUS FORMALDEHYDE

[75] Inventor: John F. Knifton, Austin, Tex.

[73] Assignee: Texaco Inc., White Plains, N.Y.

[21] Appl. No.: 663,281

[22] Filed: Oct. 22, 1984

[51] Int. Cl.$^4$ .................... C07C 29/00; C07C 31/20
[52] U.S. Cl. .................... 568/852; 568/678; 568/680
[58] Field of Search .................... 568/852

[56] References Cited

U.S. PATENT DOCUMENTS 4,356,332 10/1982 Knifton .................... 568/852
4,362,820 12/1982 Kaplan .................... 518/700

FOREIGN PATENT DOCUMENTS 90522 5/1983 Japan.

OTHER PUBLICATIONS

Herman, "Catalytic Conversions of Synthesis Gas and Alcohols to Chemicals, pp. 221–223, based mainly on a Symposium held Apr. 6–8, 1983.

Primary Examiner—J. E. Evans
Attorney, Agent, or Firm—Jack H. Park; Kenneth R. Priem; Cynthia L. Kendrick

[57] ABSTRACT

This invention relates to the manufacture of ethylene glycol and more particularly to a low pressure process for making ethylene glycol comprising reacting synthesis gas, i.e. a mixture of carbon monoxide and hydrogen, plus formaldehyde in the presence of a homogenous liquid catalyst containing an effective amount of cobalt-containing compound and a silicon-containing promoter at a temperature of at least 50° C. and a pressure of at least 500 psi.

4 Claims, No Drawings

PROCESS FOR LOW PRESSURE SYNTHESIS OF ETHYLENE GLYCOL FROM SYNTHESIS GAS PLUS FORMALDEHYDE

This application is related to copending U.S. patent application Ser. Nos. 663,284, 663,280 and 663,602, filed of even date, the first two now U.S. Pat. Nos. 4,565,896 and 4,568,780, respectively.

FIELD OF THE INVENTION

This invention relates to a new process for preparing ethylene glycol. More particularly, this invention relates to a novel low pressure process for preparing ethylene glycol from syngas which comprises contacting syngas, a mixture of carbon monoxide and hydrogen, plus formaldehyde with a catalyst comprising a cobalt-containing compound and a halogen-free silicon-containing promoter in a solvent at a temperature of at least 50° C. and a pressure of from about 500 psig.

BACKGROUND OF THE INVENTION

Ethylene glycol is a chemical which has found wide use in industry. It is used, for example in the preparation of plasticizers for vinyl polymers and as a component in polyester fibers and antifreeze formulations. In view of its many uses, there is a need to find new and more economical methods for preparing ethylene glycol.

Proposed methods for making ethylene glycol involve the reaction of carbon monoxide with hydrogen in the presence of various proposed catalyst systems at elevated temperatures and pressures. For example, one of the earliest disclosed processes for making polyhydroxy compounds from readily available and inexpensive starting materials such as formaldehyde, carbon monoxide and hydrogen was disclosed in U.S. Pat. No. 2,451,333. The process comprised heating the starting materials with a reduced cobalt oxide hydrogenation catalyst under a high pressure, in excess of 100 atm. and at a temperature from about 80° C. to 300° C. Actually the examples in this patent used high pressures in the range of 500–800 atmospheres.

In Japan Kokai No. 76,128,903 (1976) to Mitsubishi a procedure is disclosed for preparing ethylene glycol by the reaction of CO, $H_2$ and HCHO with a cobalt catalyst containing a trivalent P, As or Sb compound at a temperature of about 160° C. and a pressure of about 180 Kg/cm², or approximately 2700 psi.

Similarly U.S. Pat. No. 4,144,401 uses CO, $H_2$ and formaldehyde as starting materials, but they are reacted in the presence of an alcohol solvent and a catalytic amount of rhodium or a rhodium-containing compound at a moderate temperature and pressure. Of course use of rhodium in a catalyst makes it expensive for commercial purposes. Methanol is also produced in substantial amounts in this process.

In U.S. Pat. No. 4,200,765 there is disclosed a process for preparing glycol aldehyde by reacting formaldehyde, hydrogen and carbon monoxide in an aprotic solvent at elevated temperatures and superatmospheric pressures in the presence of a rhodium catalyst with subsequent conversion of the glycol aldehyde to ethylene glycol by hydrogenation.

Japan Kokai No. 82,118,527 (1981) to Mitsubishi discloses the use of a ruthenium-based catalyst with a trivalent phosphorous compound to convert formaldehyde, CO and $H_2$ into ethylene glycol. The selectivity to ethylene glycol is not specified.

Japan Kokai No. 82,130,940 (1981) to Mitsui Petrochemicals employs a rhodium compound and an alkali metal compound. Again selectivity to ethylene glycol is not specified.

In U.S. Pat. No. 4,362,820 only carbon monoxide and hydrogen, without formaldehyde are used as starting materials for conversion to ethylene glycol via a catalyst comprising a cobalt-containing compound and a large excess of organosilicon compound. In most of the examples an operating temperature range of 250°–270° C. is employed, coupled with pressures of about 4000–8000 psi. Weight ratios of ethylene glycol to methanol were typically Ca. 2:1.

Additional Japanese applications disclose the use of a solution of formalin, carbon monoxide and hydrogen to produce ethylene glycol in the presence of a cobalt catalyst. See Japanese Application No. 197909 to Agency of Ind. Sci. Tech. In Jap. Application No. 188137 to the same agency, ethylene glycol is produced by reacting CO and hydrogen optionally with formaldehyde in the presence of a cobalt carbonyl and a phenol and/or alkylphenol.

Japanese Application No. 004782 (1981) to Mitsubishi discloses a process for producing ethylene glycol from formaldehyde, CO and $H_2$ in the presence of a catalyst containing ruthenium and a trivalent organo-phosphorous compound.

Finally in Japan Kokai Tokyo Koho No. JP 57,130,933 to Mitsubishi, acetals are reacted with CO and H in the presence of a cobalt-iodine catalyst system to produce ethylene glycol.

Many of these processes require the use of high pressures (particularly in the absence of an added formaldehyde source), some use expensive rhodium-containing compounds; and in most the selectivities for ethylene glycol are not very substantial.

The disclosure of a process for producing ethylene glycol from simple starting materials such as syngas (i.e. carbon monoxide and hydrogen) and formaldehyde by reacting the starting materials in the presence of a catalyst compound which would be relatively inexpensive even on a commercial sale and which could be reacted at low temperatures and pressures therefore allowing for less expense in construction of reactors, etc. would be an advance in the art, especially if the selectivity for ethylene glycol were better than found in previous work.

SUMMARY OF THE INVENTION

This invention concerns a process for making ethylene glycol comprising contacting a mixture of synthesis gas, i.e., carbon monoxide and hydrogen plus formaldehyde with a catalyst comprising a cobalt-containing compound and a silicon-containing compound and heating the resultant mixture at a temperature of at least 100° C. and a pressure of at least 500 psi and preferably less than 4000 psi for sufficient time to produce the desired ethylene glycol. By using this catalyst system one can obtain substantial selectivity in the formation of ethylene glycol, the process can be operated at lower temperatures and pressures and the use of extreme conditions and expensive catalyst compounds required in many of the prior known processes can be avoided.

The process of the invention as far as the formation of the desired ethylene glycol is concerned may be represented by the following equation:

$$CO + 2H_2 + HCHO \rightarrow HOCH_2CH_2OH + H_2O \qquad (1)$$

Typical concentrations of ethylene glycol in the crude liquid product range up to 8.6 wt %, typical yields of ethylene glycol (basis formaldehyde charged) range up to 27 mole %. Total glycol products may comprise up to 18.9 wt % of the crude liquid and the yields of total glycol products (basis formaldehyde charged) may exceed 50 mole %.

DETAILED DESCRIPTION OF THE INVENTION

In the operation of the process of the invention, ethylene glycol is prepared from a synthesis gas mixture of carbon monoxide and hydrogen plus formaldehyde by a process comprising the following steps:

(a) contacting said mixture of carbon monoxide, hydrogen and formaldehyde with a catalyst comprising a cobalt-containing compound and a silicon-containing compound;

(b) heating said mixture to a temperature of at least 50° C. under a pressure greater than 500 psi and less than 4000 psi with sufficient carbon monoxide and hydrogen to satisfy the above-noted stoichiometry of the desired ethylene glycol synthesis until substantial formation of the desired ethylene glycol has been achieved; and (c) preferably isolating said ethylene glycol contained therein.

In order to present the inventive concept of the present invention in the greatest possible detail, the following supplementary disclosure is submitted. The process of the invention is practiced as follows:

As noted, the new catalyst system used in the process of the invention contains a cobalt-containing compound and a silicon-containing promoter. The cobalt compound to be used may be chosen from a wide variety of organic and inorganic compounds, complexes, etc. It is only necessary that the catalyst employed contain the cobalt in any of its ionic states.

The cobalt-containing compound employed may take many different forms. For instance the cobalt may be added to the reaction mixture in an oxide form as in the case of, for example, cobalt(II) oxide, (CoO) or cobalt-(II,III) oxide ($Co_3O_4$). Alternatively, it may be added as the salt of a mineral acid, as in the case of cobalt(II) nitrate hydrate ($Co(NO_3)_2 \cdot 6H_2O$), cobalt(II) phosphate, cobalt(II) sulfate, etc. or as the salt of a suitable organic carboxylic acid, for example, cobalt(II) formate, cobalt-(II) acetate, cobalt(II) propionate, cobalt naphthenate, or bonded to a carbonyl-containing ligand as in the case of cobalt acetylacetonate, etc. The cobalt may also be added to the reaction zone as a carbonyl or hydridocarbonyl derivative. Here, suitable examples include dicobalt octacarbonyl, ($Co_2(CO)_8$), cobalt hydridocarbonyl, ($HCo(CO)_4$) and substituted carbonyl species such as the organophosphorus cobalt carbonyls like $HCo(CO)_3(Bu_3P)$.

Preferred cobalt-containing compounds include oxides of cobalt, cobalt salts of mineral acids, cobalt salts of organic carboxylic acids and cobalt carbonyl or hydridocarbonyl derivatives. Among these, particularly preferred are dicobalt octacarbonyl, cobalt(II) oxide, cobalt(II) nitrate, cobalt acetylacetonate and cobalt(II) acetate.

The silicon-containing promoter employed in the practice of this invention may also take many different forms. Generally, the promoter should contain at least one bond between a silicon atom and a carbon atom, but suitable organosilicon compounds may comprise mono-, di-, tri- and tetraorgano groups bonded to silicon. Each organo group may be an alkyl, aryl or aryalkyl moiety, having one to 20 carbon atoms. The silicon-containing promoter may also contain silicon-oxygen bonds, and preferred promoters are halogen-free silanes containing at least one silicon-hydrogen bond per molecule.

Typical of suitable organosilicon compounds that are suitable for use in the process of equation (1) include trialkylsilanes, such as triethylsilane ($Et_3SiH$), tricyclohexylsilane [$(C_6H_{11})_3SiH$], trimethylsilane, tri-n-hexylsilane and methyl, diethylsilane ($MeEt_2SiH$), as well as dimethylethylsilane and the tripropylsilanes, the dialkylsilanes such as diethylsilane ($Et_2SiH_2$) and dimethylsilane, the tetraalkylsilanes such as tetramethylsilane and tetraethylsilane, the arylsilanes such as triphenylsilane ($Ph_3SiH$), diphenylsilane and hydroxytriphenylsilane, as well as the alkoxysilanes such as triethoxysilane [$(EtO)_3SiH$], phenyltriethoxysilane, tetraethoxysilane and tetramethoxysilane. Less satisfactory are the halogenated organosilanes such as chlorotrimethylsilane, dimethylsilane chloride ($Me_2SiHCl$), chlorotriphenylsilane, dichlorodimethylsilane ($Me_2SiCl_2$), chlorotriethylsilane, and iodotrimethylsilane.

Other suitable organosilicon promoters containing at least one silicon-hydride bond, and more than one silicon atom per molecule, include:

$$H_3SiCH_2SiH_3$$
$$H_3SiCH_2CH_2SiH_3$$
$$CH_3SiH_2CH_2SiH_3$$

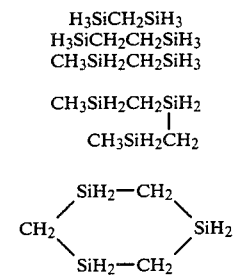

Suitable silanes containing more than one silicon-hydride bond per molecule are exemplified by:

$$(CH_2=CHCH_2)_2SiH_2$$

$$(CH_3)(CH_2=CHCH)SiH_2$$
$$|$$
$$CH_3$$

$$(C_2H_5)_2SiH_2$$

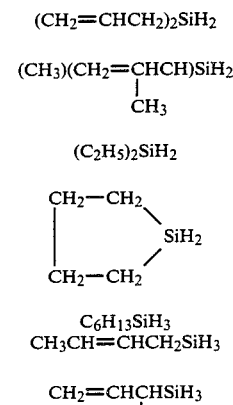

$$C_6H_{13}SiH_3$$
$$CH_3CH=CHCH_2SiH_3$$

$$CH_2=CHCHSiH_3$$
$$|$$
$$CH_3$$

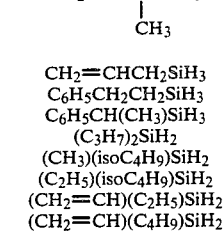

Also effective as silicon-containing promoters in the practice of this process are siloxanes and polyalkylsiloxanes. These may include hexaethyldisiloxane, hexamethylcyclotrisiloxane, octamethylcyclotetrasiloxane, hexamethyldisiloxane, tetramethyldisiloxane (Me$_2$HSi-OSiHMe$_2$), methylhydrocyclosiloxane, as well as alkylsiloxane polymers of the type:

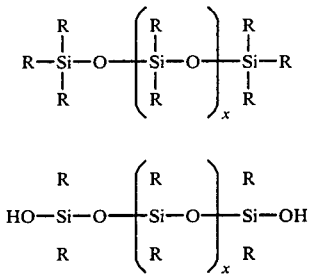

wherein R is one or different alkyl groups containing 1 to 6 carbon atoms.

Equally useful are the higher M.W. tetraalkylsilanes and tetraalkoxysilanes wherein each alkyl or alkoxy group contains 1 to 20 carbon atoms, and each alkyl group may have the same or different carbon number.

Preferred organosilane compounds include triethylsilane, triphenylsilane, trimethylsilane, diphenylsilane, tricyclohexylsilane, tetramethylsilane, tetraethylsilane, hydroxytriphenylsilane, diethylsilane and tripropylsilane.

As characterized above, this process is operated as a homogeneous liquid phase mixture. The process is typically carried out in a solvent. The solvent may be solid at room temperature but should at least, in part, be a liquid under the conditions of reaction. The solvent is selected such that the solvent is capable of maintaining the cobalt catalyst in the homogeneous liquid phase mixture throughout the reaction.

A variety of substantially inert aliphatic hydrocarbon solvents are useful in the process of this invention including aliphatic hydrocarbon and oxygenated aliphatic hydrocarbon solvents. Suitable oxygenated aliphatic hydrocarbon solvents are compounds composed only of carbon, hydrogen and oxygen and those in which the only oxygen atoms present are in ether groups, ester groups, ketone carbonyl groups or hydroxyl groups of alcohols. Generally, the oxygenated hydrocarbon will contain 3 to 12 carbon atoms and preferably a maximum of 3 oxygen atoms. The solvent must be substantially inert under reaction conditions, it may be relatively non-polar and it must be one which has a normal boiling point of at least 65° C. at atmospheric pressure, and preferably, the solvent will have a boiling point greater than that of methanol and other oxygen-containing reaction products so that recovery of the solvent by distillation is facilitated.

Preferred ester type solvents are the aliphatic and acylic carboxylic acid monoesters as exemplified by butyl acetate, methyl valerate, isopropyl iso-butyrate, and propyl propionate as well as dimethyl adipate. Useful alcohol-type solvents include monohydric alcohols such as cyclohexanol, 1-hexanol, 2-hexanol, neopentanol, 2-octanol, etc. Suitable ketone-type solvents include, for example, cyclic ketones such as cyclohexanone, 2-methylcyclohexanone, as well as acylic ketones such as 2-pentanone, butanone, acetophenone, etc. Ethers which may be utilized as solvents include cyclic, acyclic and heterocyclic materials. Preferred ethers are the aliphatic cyclic ethers as illustrated by 1,4-dioxane and 1,3-dioxane. Other suitable ether solvents include isopropyl propyl ether, diethylene glycol dibutyl ether, dibutyl ether, ethyl butyl ether, tetraethylene glycol dimethyl ether, triethylglycol dimethyl ether, Bis(2-ethoxyethyl)ether, tetrahydrofuran, etc. The most useful solvents of all of the above groups include the ethers as represented by monocyclic, ethers such a 1,4-dioxane or p-dioxane, etc. Hydrocarbon solvents, such as hexane, heptane, decane, dodecane, tetradecane, etc. may also be suitable solvents for use in this invention under certain circumstances.

The quantity of cobalt-containing compound and the silicon-containing compound to be used in the process of the invention may vary. The process is conducted in the presence of a catalytically effective quantity of the active cobalt-containing compound and the active silicon-containing compound which gives the desired product in a reasonable yield. The reaction proceeds when employing as little as about $10^{-2}$ weight percent, and even lesser amounts of the cobalt-containing compound, together with as little as about $10^{-2}$ weight percent of the silicon-containing compound based on the total weight of the reaction mixture. The upper concentration is dictated by a variety of factors including catalyst cost, partial pressures of carbon monoxide and hydrogen, operating temperature, etc. A cobalt-containing compound concentration of from about $10^{-2}$ to about 30 weight percent in conjunction with a silicon-containing compound concentration of from about $10^{-2}$ to about 30 percent, based on the total weight of the reaction mixture is generally desirable in the practice of this invention.

Particularly superior results are obtained when the above-noted components of the catalyst system are combined as follows on a molar basis: cobalt-containing compounds to silicon-containing compound of 1:0.1 to 1:10 (Co:Si). In contrast to the direct synthesis of ethylene glycol from synthesis gas (as for example in U.S. Pat. No. 4,367,820) normally conducted at higher pressures than in this work, the use of a silicon-containing compound in large excess over the cobalt-containing compound, leads to a substantial supression of glycol yield from syngas plus formaldehyde (See, for example, Table I, Example V).

The temperature range which can be employed in the process of the invention may vary over a considerable range depending upon experimental factors, including the choice of catalyst, pressure and other variables. A preferred range of operability is from about 50° C. to about 350° C. when superatmospheric pressures of syngas are employed. A narrower range of about 100° C. to 220° C. represents a particularly preferred temperature range.

The pressure employed may also vary over a considerable range, but in most cases is at least above 500 psig. A preferred operating range varies from about 1000 psig to about 4000 psig, although pressures above 4000 psig also provide useful yields of the desired product. The pressures referred to herein represent the total pressure generated by all the reactants, although they are substantially due to the carbon monoxide and hydrogen fractions. In the presence of formaldehyde, the total pressures required for glycol syntheses using cobalt/silane-promoted catalyst systems are normally lower than those pressures required for direct glycol production from CO/H₂ (See, for example, U.S. Pat. No. 4,367,820). This may in part be due to the fact that the formation of formaldehyde from synthesis gas (eq 2) is thermodynamically unfavorable under the range of operating conditions disclosed in these syntheses (See Stanford Research Institute Report #23A (Dec. 1978) entitled "Formaldehyde").

$$CO + H_2 \rightleftharpoons HCHO \qquad (2)$$

The relative amounts of carbon monoxide and hydrogen which can be initially present in the syngas mixture are variable, and these amounts may be varied over a wide range. In general, the mole ratio of CO:H₂ is in the range from about 20:1 to about 1:20, and preferably from about 5:1 to 1:5, although ratios outside these ranges may also be employed with good results. Particularly in continuous operations, but also in batch experiments, the carbon monoxide-hydrogen gaseous mixture may also be used in conjunction with up to 50% by volume of one or more other gases. These other gases may include one or more inert gases such as nitrogen, argon, neon, and the like, or they may include gases that may, or may not, undergo reaction under carbon monoxide hydrogenation conditions, such as carbon dioxide, hydrocarbons, such as methane, ethane, propane, and the like, ethers, such as dimethyl ether, methylethyl ether and diethyl ether, alkanols, such as methanol, and the like.

In all these synthesis in order to achieve a high degree of selectivity the amount of carbon monoxide, hydrogen and formaldehyde present in the reaction mixture should be sufficient to at least satisfy the stoichiometry of the desired formation of ethylene glycol as shown in equation (1) above. Excess carbon monoxide and/or hydrogen over the stoichiometric amount may be present, if desired.

The most desired product of this synthesis, ethylene glycol (EG) will be formed in significant quantities (up to Ca. 9 wt % concentration in the crude liquid product) and up to Ca. 27 mole % selectivity (basis total formaldehyde charged) using the cobalt-silicon promoted catalyst system of this invention. Also formed are significant amounts of diethylene glycol (DEG), propylene glycol (PG), together with derivatives such as the ethylene glycol monoalkyl ethers (e.g. ethylene glycol monomethyl ether, EGMME). Selectivity to total glycol products (EG+DEG+PG+EGMME) may exceed 50 mole %. Lower monohydric alcohols, methanol and ethanol are also present in the crude liquid product mix. Each of these product oxygenates, including ethylene glycol, monohydric alcohols and other by-products can be recovered from the reaction mixture by conventional means, e.g. fractional distillation in vacuo.

The novel process of the invention can be conducted in a batch, semi-continuous or continuous manner. The catalyst can be initially introduced into the reaction zone batchwise, or it may be continuously or intermittently introduced into such a zone during the course of the synthesis reaction. Operating conditions can be adjusted to optimize the formation of the desired ethylene glycol product, and said material may be recovered by methods known to the art, such as distillation, fractionation, extraction and the like. A fraction rich in the catalyst components may then be recycled to the reaction zone, if desired, and additional product generated.

The products have been identified in this work by one or more of the following analytical procedures: viz, gas-liquid phase chromatography (glc), gas chromatography/infrared spectroscopy (GC/IR), nuclear magnetic resonance (nmr) and elemental analyses, or a combination of these techniques. Analyses have, for the most part, been by parts by weight; all temperatures are in degrees centigrade and all pressures in pounds per square inch (psi).

The yield of ethylene glycol in each synthesis (mole %) is estimated basis equation 1 using the formula:

$$\frac{\text{Total Ethylene Glycol Produced (mmole)}}{\text{Total formaldehyde charged (mmole)}} \times 100$$

Total glycol yield (mole %) are estimated basis:

$$\frac{\text{Total Glycol Products Generated }[EG + EGMME + PG + DEG \text{ (mmole)}]}{\text{Total Formaldehyde charged (mmole)}} \times 100$$

Total product yield (wt %) is estimated basis:

$$\frac{(\text{Total Liquid } + \text{ Solid Product, g}) - (\text{Catalyst } + \text{ Solvent } + \text{ Formaldehyde Charged, g})}{(\text{Catalyst } + \text{ Solvent } + \text{ Formaldehyde Charged, g})} \times 100$$

To illustrate the process of the invention, the following examples are given. It is to be understood, however, that the examples are given in the way of illustration and are not to be regarded as limiting the invention in any way.

EXAMPLE I

A 450 ml capacity reactor with glass liner was charged with a mixture of dicobalt octacarbonyl (12.0 mmole Co, 2.052 g), triethylsilane (24.0 mmole Si, 2.790 g) and paraformaldehyde (0.1 mole, 3.0 g) in p-dioxane (15.0 g). The mixture was flushed with nitrogen, the reactor sealed, flushed with synthesis gas, pressured to 2700 psig with CO/H₂ (1:2), and heated to 160° C. with agitation. After four hours, the reactor was allowed to cool, the gas pressure (2500 psig) noted, and the excess gas sampled and vented. 25.3 g of brown liquid product was recovered, there was no solid precipitate at this stage.

Analysis (glc and Karl Fischer titration) of the liquid product shows it to contain:
- 8.1 wt % ethylene glycol (EG)
- 3.3 wt % ethylene glycol monomethyl ether (EGMME)
- 1.0 wt % propylene glycol (PG)
- 6.5 wt % diethylene glycol (DEG)
- 2.5 wt % methanol
- 0.8 wt % ethanol
- 66.5 wt % p-dioxane solvent
- 2.2 wt % water Cobalt recovery in the liquid product was estimated to be 87% of that originally charged.

Analysis of the gas sample shows it to contain:
- 67% hydrogen
- 33% carbon monoxide <0.1% carbon dioxide
<0.1% methane
Estimated yield of ethylene glycol is 1.66 g (26.8 mmole).
Estimated yield of ethylene glycol (basis formaldehyde charged) is 27 mole %.
Estimated yield of total glycol products (EG+PG+DEG+EGMME) is 51 mole %.
Total product yield is 11 wt %.

EXAMPLES II–XI

Examples II–XI were conducted in the same way as ethylene glycol from synthesis gas plus formaldehyde, including triethylsilane, triphenylsilane, tricyclohexylsilane, diphenylsilane and hydroxytriphenyl silane.

(b) For the dicobalt octacarbonyl-triethylsilane catalyst combination the highest ethylene glycol yields are realized at an initial Co:Si mole ratio of 1:2 (Example I).

(c) Ethylene glycol yields are substantially reduced, product yields are lower, and cobalt recovery is poorer, when a large excess of silane promoter ($Et_3SiH$) is added to solubilize the dicobalt octacarbonyl catalyst precursor (see Example V), and the initial Si:Co molar ratio is >10.

TABLE I

HCHO + $CO/H_2$ GLYCOL

Liquid Product Composition (Wt. %)

| Example | Composition | $CH_2OH$–$CH_2OH$ | $CH_2OCH_3$–$CH_2OH$ | P.G. | DEG | MeOH | EtOH | $H_2O$ | Cobalt[b] Recov. (%) | Product[b] Yield (%) |
|---|---|---|---|---|---|---|---|---|---|---|
| II | $Co_2(CO)_8$—$2Et_3SiH$ | 6.2 | 2.3 | 0.9 | 5.5 | 1.6 | 1.0 | 7.6 | >99 | 15 |
| III | $Co_2(CO)_8$—$Et_3SiH$ | 5.0 | 1.9 | 0.8 | 3.8 | 1.4 | 1.0 | 5.0 | >99 | 15 |
| IV | $Co_2(CO)_8$—$8Et_3SiH$ | 1.4 | 1.8 | 0.4 | 2.2 | 2.1 | 0.3 | 4.3 | 76 | 11 |
| V | $Co_2(CO)_8$—$22Et_3SiH$ | 1.3 | 1.1 | 0.3 | 0.3 | 2.4 |  | 0.1 | 45 | 7 |
| VI | $Co_2(CO)_8$—$4Ph_3SiH$ | 1.4 / 6.1 | 4.7 / 5.8 | 0.5 / 0.7 | 3.1 / 4.7 | 2.0 / 3.6 | 0.8 / 1.0 | 3.0 | 92 | 8[c] |
| VII | $Co_2(CO)_8$—$4(C_6H_{11})_3SiH$ | 0.1 / 7.1 | 0.9 / 4.1 | / 0.4 | 1.8 / 8.1 | 1.1 / 3.0 | 0.3 / 0.9 | 5.7 | >99 | 8[c] |
| VIII | $Co_2(CO)_8$—$4(EtO)_3SiH$ | 6.6 | 1.9 | 0.3 | 5.0 | 1.7 | 11.4 | 2.9 | d | 14[d] |
| IX | $Co_2(CO)_8$—$4Ph_2SiH_2$ | 1.7 / 7.3 | 2.9 / 4.8 | 0.2 / 0.5 | 2.2 / 3.6 | 1.9 / 3.9 | 0.4 / 0.8 | 2.4 / 5.7 | >99 | 11[c] |
| X | $Co_2(CO)_8$—$4Ph(EtO)_3Si$ | 8.6[e] | 0.7 | 0.3 | 3.0 | 0.7 | 7.8 | 4.6 | >99 | 16 |
| XI | $Co_2(CO)_8$—$4Ph_3SiOH$ | 3.9 / 11.3 | 5.3 / 4.6 | 0.2 / 0.7 | 3.8 / 6.7 | 1.0 / 1.7 | 0.7 / 1.1 | 2.3 / 10.2 |  | 13[c] |

[a]Reaction charge: Co, 12.0 mmole; Si, 12.0 mmole; $H_2CO$, 100 mmole; p-dioxane, 15.0 g.
Run conditions: 160° C.; 2700 psi $CO/H_2$ (1:2) initial pressure; 4 hours.
[b]Cobalt recovery estimated basis cobalt recovered in solution at the end of run versus cobalt originally charged; total product yield calculated as described in text.
[c]Two-phase liquid product.
[d]Low liquid yield, considerable quantity of solid product.
[e]Glycol present as ethylene glycol monoethyl ether.

Example I. In every example dicobalt octacarbonyl was the cobalt-containing catalyst used and p-dioxane was employed as the solvent. Different halogen-free silicon-containing compounds were employed and the results in terms of weight percent of ethylene glycol, propylene glycol, diethylene glycol, glycol monomethyl ether etc. in the crude liquid product are shown in Table I.

It may be seen from an inspection of Table I that:

(a) A variety of halogen-free silicon-containing compounds are effective promoters for the synthesis of

COMPARATIVE EXAMPLES XII THROUGH XVII

Examples XII through XVII were conducted with the same reaction charge as Example I as well as with the same set of operating conditions. In these examples, however, halogen-containing silicon compounds were used. It is noted that the weight percent of ethylene glycol in the product is much less.

TABLE II

HCHO + $CO/H_2$ → GLYCOL

Liquid Product Composition (Wt. %)

| Example | Catalyst Composition[a] | $CH_2OH$–$CH_2OH$ | $CH_2OCH_3$–$CH_2OH$ | P.G. | DEG | MeOH | EtOH | $H_2O$ | Cobalt Recov. (%) | Product[b] Yield (wt %) |
|---|---|---|---|---|---|---|---|---|---|---|
| XII | $Co_2(CO)_8$—$4Me_3SiCl$ | 0.1 | 0.4 |  |  | 0.6 |  | 1.5 | <5 | None[c] |
| XIII | $Co_2(CO)_8$—$4Me_2SiHCl$ | 0.6 / 0.5 |  | 0.2 / 0.3 | 0.3 / 0.4 | 1.4 / 2.7 |  | 1.6 / 8.3 | <5 | None[d,c] |
| XIV | $Co_2(CO)_8$—$4Ph_3SiCl$ | 0.3 | 2.6 | 0.2 |  | 0.7 |  |  | <5 | None[c] |
| XV | $Co_2(CO)_8$—$4Me_2SiCl_2$ | 0.2 | 0.1 |  |  |  |  |  | <5 | None[c] |
| XVI | $Co_2(CO)_8$—$4Et_3SiCl$ | 0.1 | 0.1 |  |  | 0.8 |  | 0.7 | <5 | None[c] |
| XVII | $Co_2(CO)_8$—$4Me_3SiI$ |  | 0.1 |  |  | 0.1 |  | 0.8 |  | None |

[a]Reaction charge and operating conditions as per Table I.
[b]Product yield calculated basis weight of catalyst-formaldehyde solution originally charged.
[c]Low liquid yield, considerable quantity of solid product.
[d]Two-phase liquid product.

COMPARATIVE EXAMPLE XVIII

Following the procedures of Example I, the reactor was charged with a mixture of dicobalt octacarbonyl (12.0 mmole Co, 2.052 g), triethylsilane (129 mmole Si, 15.0 g) and paraformaldehyde (100 mmole, 3.0 g). After pressuring to 2700 psig with CO/H$_2$ (1:2) and heating to 160° C./ with agitation for 4 hours, the reactor was allowed to cool, the gas pressure (2525 psig) noted, and the excess gas sampled and vented. 23.2 g of brown liquid suspension was recovered.

Analysis of the liquid product fraction shows it to contain:
0.1 wt % ethylene glycol
0.5 wt % ethylene glycol monomethyl ether
1.1 wt % methanol
62.5 wt % p-Dioxane solvent
0.9 wt % water Analysis of the gas sample shows it to contain:
68% hydrogen
31% carbon monoxide This example illustrates the poor yields of ethylene glycol obtained with the cobalt-silane catalyst system when the desired preparation from syngas and formaldehyde is conducted:

(a) At initial Si:Co molar ratios of >10.
(b) In the absence of added aliphatic ether solvent.

EXAMPLE XIX

Following the procedures of Example I, the reactor was charged with a mixture of dicobalt octacarbonyl (12.0 mmole Co, 2.052 g), tetramethylsilane (24.0 mmole, 2.118 g), paraformaldehyde (0.1 mole, 3.0 g) and p-Dioxane (15.0 g). After pressuring to 2700 psig with CO/H$_2$ (1:2), and heating to 160° C. with agitation for 4 hours, the reactor was allowed to cool, the gas pressure (1700 psig) noted, and the excess gas sampled and vented. 23.8 g of brown liquid product was recovered, there was no solid precipitate at this stage.

Analysis of the liquid product shows it to contain:
4.8 wt % ethylene glycol
1.0 wt % ethylene glycol monoethyl ether
0.7 wt % propylene glycol
1.8 wt % diethylene glycol
0.5 wt % methanol
0.5 wt % ethanol
78.5 wt % p-Dioxane solvent
7.9 wt % water Cobalt recovery in the liquid product was estimated to be >99%.

Analysis of the gas sample shows it to contain:
66% hydrogen
33% carbon monoxide
0.1% carbon dioxide

What is claimed is:

1. A process for making ethylene glycol from synthesis gas, i.e., a mixture of carbon monoxide and hydrogen, and formaldehyde which comprises reacting said synthesis gas and formaldehyde in the presence of a catalyst comprising an effective amount of cobalt carbonyl compound and a halogen-free organosilicone compound from the group consisting of triethysilane, triphenylsilane, hydroxytriphenylsilane, diphenylsilane, tricyclohexylsilane and tetramethylsilane in the presence of a monocyclic ether at a temperture of from 100° C. to 220° C. and a pressure of from about 1000 psi to less than 4000 psi, wherein the molar ratio of cobalt to silicon in the added cobalt-containing compound and the silicon-containing promoter is in the range from 1:0.1 to 1:10.

2. The process of claim 1, wherein the cobalt-containing compound is dicobalt octacarbonyl.

3. The process of claim 1 in which the aliphatic, oxygenated hydrocarbon solvent is p-dioxane.

4. A process for making ethylene glycol which comprises reacting a mixture of carbon monoxide and hydrogen plus formaldehyde in the presence of a catalyst comprising dicobalt octacarbonyl and a triethylsilane promoter solubilized in p-dioxane at a temperature of about 160° C. and an initial pressure of about 2500 psi, wherein the molar ratio of cobalt to silicon in the added cobalt-containing compound and the silicon-containing promoter is in the range from 1:0.1 to 1:10.

* * * * *